(12) United States Patent
Bartholomeusz et al.

(10) Patent No.: US 12,649,055 B2
(45) Date of Patent: Jun. 9, 2026

(54) SKIN PATCH FOR RF ENERGY-BASED TREATMENT DEVICE, A RF ENERGY-BASED TREATMENT DEVICE USING SAME, A METHOD OF CONTROLLING THE SAME, AND A RF ENERGY-BASED SKIN TREATMENT METHOD

(71) Applicant: LUTRONIC CORPORATION, Goyang-si (KR)

(72) Inventors: James Bartholomeusz, Beverly Hills, CA (US); Kwang Chon Ko, Paju-si (KR)

(73) Assignee: LUTRONIC CORPORATION, Goyang-si (KR)

( * ) Notice: Subject to any disclaimer, the term of this patent is extended or adjusted under 35 U.S.C. 154(b) by 1017 days.

(21) Appl. No.: 17/642,202

(22) PCT Filed: Nov. 11, 2019

(86) PCT No.: PCT/KR2019/015237
§ 371 (c)(1),
(2) Date: Mar. 10, 2022

(87) PCT Pub. No.: WO2021/095889
PCT Pub. Date: May 20, 2021

(65) Prior Publication Data
US 2022/0313988 A1 Oct. 6, 2022

(51) Int. Cl.
*A61N 1/06* (2006.01)
*A61B 18/00* (2006.01)
(Continued)

(52) U.S. Cl.
CPC .............. *A61N 1/06* (2013.01); *A61N 1/328* (2013.01); *A61N 1/40* (2013.01); *A61B 2018/00452* (2013.01); *A61B 2018/00875* (2013.01)

(58) Field of Classification Search
CPC . A61N 1/06; A61N 1/328; A61N 1/40; A61N 1/0492; A61N 1/36017; A61B 2018/00452; A61B 2018/00875
See application file for complete search history.

(56) References Cited

U.S. PATENT DOCUMENTS 5,879,346 A * 3/1999 Waldman ............. A61B 18/203
606/9
6,413,255 B1 * 7/2002 Stern ........................ A61N 5/04
606/41
(Continued)

FOREIGN PATENT DOCUMENTS

JP 2002-537939 A 11/2002
JP 6170105 B2 7/2017
(Continued)

OTHER PUBLICATIONS

"Lifting secretly provided to celebrities of Hollywood and Korea— Thermage CPT", May 12, 2018, Korea.
(Continued)

*Primary Examiner* — Adam Z Minchella
*Assistant Examiner* — Ashleigh Lauren Kern

(57) ABSTRACT

The present invention relates to: a skin patch for an RF energy-using treatment device, the skin patch which has one surface in contact with the skin and has the other surface that is usable by making contact with an electrode of the RF energy-using treatment device, and which comprises a marker so as to guide treatment of the RF energy-using treatment device; an RF energy using treatment device using the skin patch; a control method therefor; and an RF
(Continued)

energy-using skin treatment method. The skin patch for an RF energy-using treatment device, the RF energy-using treatment device using same, the control method therefor and the RF energy-using skin treatment method, according to the present invention, can guide the treatment location of a user from the patch attached to the skin, and control RF energy so as to improve treatment precision.

13 Claims, 33 Drawing Sheets

(51) Int. Cl.
| | |
|---|---|
| *A61N 1/32* | (2006.01) |
| *A61N 1/40* | (2006.01) |

(56) References Cited

U.S. PATENT DOCUMENTS

| | | | |
|---|---|---|---|
| 9,216,058 B2 | 12/2015 | Spertell | |
| 9,610,123 B2 | 4/2017 | Cornil | |
| 2006/0009763 A1 | 1/2006 | Goble et al. | |
| 2007/0198004 A1 | 8/2007 | Altshuler et al. | |
| 2010/0217161 A1* | 8/2010 | Shalgi | A61B 5/6843 |
| | | | 601/2 |

| | | | |
|---|---|---|---|
| 2015/0182757 A1* | 7/2015 | Levine | G16H 20/30 |
| | | | 606/9 |
| 2016/0089535 A1 | 3/2016 | Mohammadi et al. | |
| 2016/0346529 A1* | 12/2016 | Cazares Delgadillo | |
| | | | A61N 1/327 |

FOREIGN PATENT DOCUMENTS

| | | | | |
|---|---|---|---|---|
| KR | 10-2011-0000790 | A | | 1/2011 |
| KR | 10-2013-0122948 | A | | 11/2013 |
| KR | 10-2016-0041830 | A | | 4/2016 |
| KR | 10-2017-0023776 | A | | 3/2017 |
| KR | 20170023776 | A | * | 3/2017 |
| KR | 20-0487659 | Y1 | | 10/2018 |
| KR | 10-2019-0000603 | A | | 1/2019 |
| KR | 10-2019-0102437 | A | | 9/2019 |
| KR | 10-2019-0111542 | A | | 10/2019 |
| WO | 2008131306 | A1 | | 10/2008 |
| WO | 2012/010861 | A1 | | 1/2012 |

OTHER PUBLICATIONS

The Extended European Search Report for European Patent Application No. 19952912.4, dated Jul. 3, 2023.

* cited by examiner tc

1

SKIN PATCH FOR RF ENERGY-BASED TREATMENT DEVICE, A RF ENERGY-BASED TREATMENT DEVICE USING SAME, A METHOD OF CONTROLLING THE SAME, AND A RF ENERGY-BASED SKIN TREATMENT METHOD

TECHNICAL FIELD

The disclosure relates to a skin patch for a radio frequency (RF) energy-based treatment device, an RF energy-based treatment device using the same, a method of controlling the same, and an RF energy-based skin treatment method, and more particularly to a treatment device capable of treating skin by a patch to be put on the skin, a method of controlling the treatment device, and a treatment method using the same.

BACKGROUND ART

A method of using radio frequency (RF) energy to treat tissue is classified into a contact treatment method that transmits the RF energy to the external surface of the tissue to treat the tissue, and an invasive treatment method that transmits the RF energy by partially or entirely inserting an RF electrode into the tissue.

Such an RF treatment method has generally been used in making an incision around a lesion of an internal organ, arresting bleeding, or the like surgical treatment. Recently, the RF treatment method has been used for wrinkle removal, scar removal, acne treatment, and the like treatment of skin lesions by transmitting the RF energy to skin through an electrode, and this is also disclosed in Korean Patent Publication No. 10-2011-0000790.

In relation to this related art, the RF treatment method for skin, in particular, facial skin has been carried out by applying one treatment procedure to a certain area of the whole treatment region having a three-dimensionally curved surface, and repeatedly performing such a treatment procedure multiple times to thereby treat the whole treatment region. In this case, there is a problem of an overlapping-treated region or an untreated region because a clear distinction between a region that needs to be treated and a region that has been treated is not made.

Further, in case of treating the facial skin, there is a problem that tissue characteristics varied depending on locations of the skin are not taken into account because uniform treatment is applied to the facial skin.

DISCLOSURE

Technical Problem

An aspect of the disclosure is to solve the foregoing problems of a conventional RF treatment device and aims to provide a skin patch for a radio frequency (RF) energy-based treatment device, an RF energy-based treatment device using the same, a method of controlling the same, and an RF energy-based skin treatment method, in which treatment location information is used to guide a user and RF energy is controlled to improve accuracy of treatment.

Technical Solution

To achieve the aspect of the disclosure, there is provided a skin patch including: a first side provided to come into contact with a skin, and a second side provided to be usable while being in contact with an electrode of a radio frequency (RF) energy-based treatment device, a marker provided to guide treatment of the RF energy-based treatment device.

Meanwhile, the marker may be provided to guide a treatment location of the RF energy-based treatment device.

Further, the marker may include a plurality of unit region markers, each size of which corresponds to an area to which treatment of the RF energy-based treatment device is applied once.

In addition, the marker may include a recognition code configured to be recognizable by the RF energy-based treatment device.

Meanwhile, the recognition code may include a plurality of unique patterns configured to display unique information based on a location of the unit region marker.

Meanwhile, the skin patch includes a dielectric.

Meanwhile, the skin patch may be divided into a plurality of regions, and at least one among the plurality of regions may be configured to have a different dielectric constant.

Further, the skin patch may be provided to be attached to a region including at least a portion of a forehead and a cheek.

The skin patch may be disposable.

Further, the skin patch may be provided to make state change in a region with which the RF energy-based treatment device comes into contact and to which treatment is applied.

Meanwhile, the state change includes change in color to be visually recognizable. In addition, there is provided an RF energy-based treatment device including: a main body; an RF generator provided in the main body; a handpiece connected to the main body, and including a plurality of electrodes configured to generate deep heat by transferring RF energy from the RF generator to a skin, and a reader unit configured to recognize a marker provided in a patch attachable to the skin; a display configured to display information; and a controller configured to control the RF generator and the display, the controller controlling at least one of the RF generator and the display based on the information recognized by the reader unit.

Meanwhile, the reader unit may be configured to recognize the marker provided in the patch attached to the skin.

In addition, the reader unit may be configured to face toward a distal end of the handpiece.

Meanwhile, the controller may be configured to identify a current treatment location based on information about the marker recognized before applying the RF energy.

Further, the controller may be configured to adjust a control parameter for the RF energy based on the identified current treatment location.

Meanwhile, the patch may include one selected among a plurality of patches having different dielectric constants, respectively.

Meanwhile, the controller may be configured to identify the dielectric constant of the patch based on the information recognized from the marker and adjust the control parameter for the RF energy.

Further, the information from the marker is recognized and the RF energy is applied, the controller may be configured to identify that treatment is completed in a treatment location based on the information from the marker.

In addition, the controller may be configured to control the display to: display a symbol corresponding to a shape of a patient's face, and display a region corresponding to a region, in which the treatment is completed, as a treatment completion region in the symbol.

Further, there is provided a method of controlling a RF energy-based treatment device, the method including: receiving information obtained by recognizing one of markers on a patch attached to a skin through a reader unit provided in a handpiece; and performing at least one of controlling output of RF energy and displaying a treatment location based on the treatment location.

Meanwhile, the controlling the output of the RF energy may include: updating with a matching parameter based on information from the maker; and generating the RF energy based on the updated parameter.

Further, the method may further include: loading a patient's information; and displaying information about a patch selected based on the patient's information.

Meanwhile, the information from the recognized marker may include information about at least one of the information about the patch and the treatment location.

Further, the updating with the matching parameter may be performed based on at least one of the patient's information, a dielectric constant of the selected patch, and the treatment location.

Meanwhile, the displaying the treatment location may include: displaying a symbol corresponding to a whole treatment region; and displaying whether the treatment has been completed, according to unit treatment areas, in which the markers are recognized, in the whole treatment region.

In addition, there is provided a radio frequency (RF) energy-based skin treatment method including: locating a skin patch to come into contact with a skin surface; recognizing a marker provided in the patch through an RF energy-based treatment device; remodeling by applying RF energy, which is adjusted based on information obtained from the recognized marker, to the skin; and taking off the patch.

Further, the RF energy-based skin treatment method may further include: receiving information about a customer targeted for treatment; and selecting one among a plurality of patches respectively having different dielectric constants, based on the information about the customer.

Meanwhile, the information obtained from the marker may include information about at least one of the patch's dielectric constant and a current treatment location.

Meanwhile, the recognizing the marker and the remodeling may be repeated for each unit treatment region corresponding to an area to which treatment is applied once.

Advantageous Effects

According to embodiments of the disclosure, a skin patch for a radio frequency (RF) energy-based treatment device, an RF energy-based treatment device using the same, a method of controlling the same, and an RF energy-based skin treatment method can guide a user's treatment location based on a patch attached to skin, and reflect a dielectric constant of a patch to control RF energy, thereby having effects on improving accuracy of treatment.

4

Figure 5:
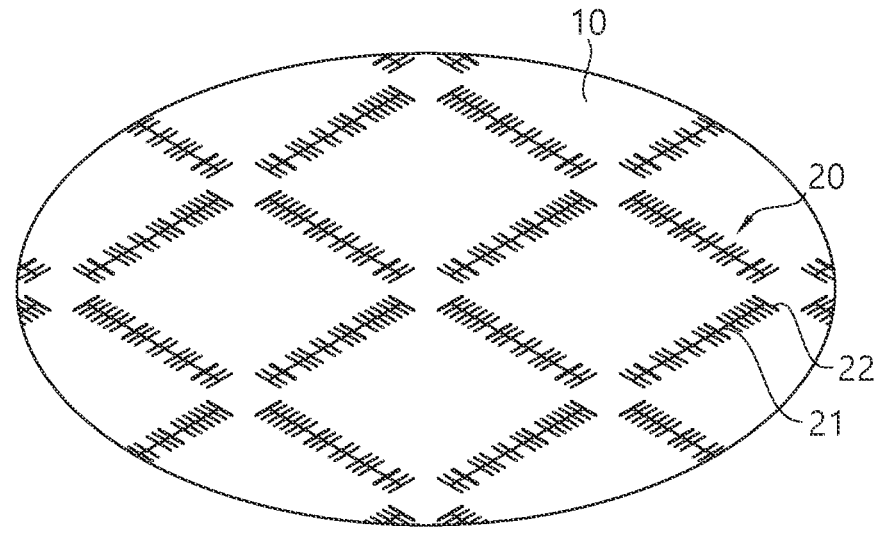

FIG. 5 shows an alternative example to the markers according to the first embodiment.

Figure 6:
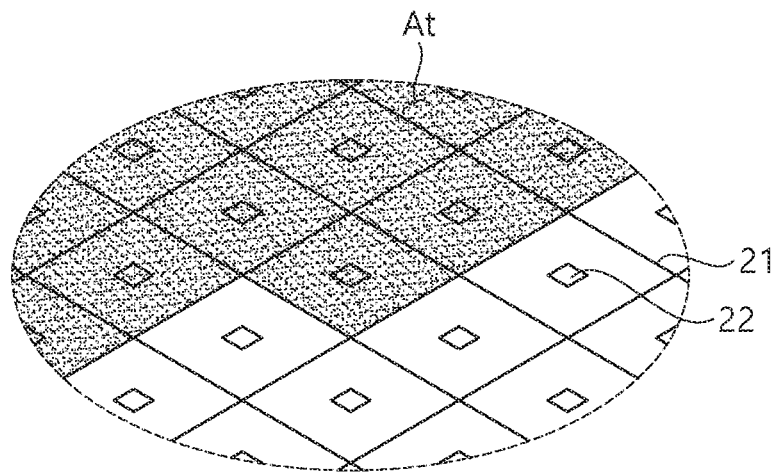

FIG. 6 is a conceptual view of another alternative example to the first embodiment.

Figure 7:
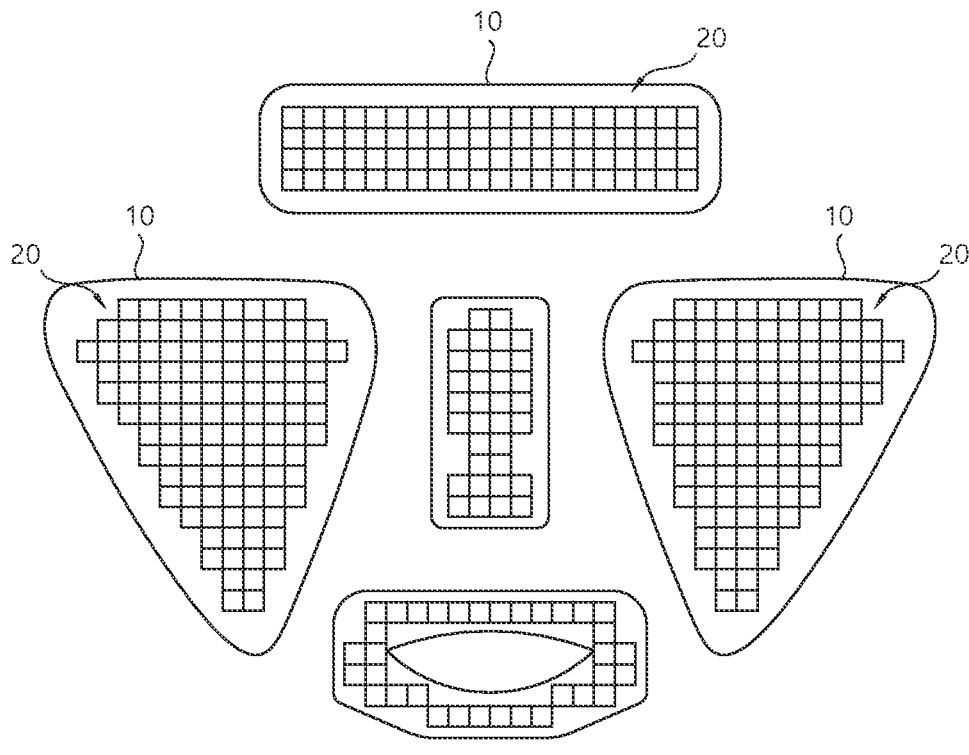

FIG. 7 is a conceptual view of an alternative example to the first embodiment.

Figure 8:
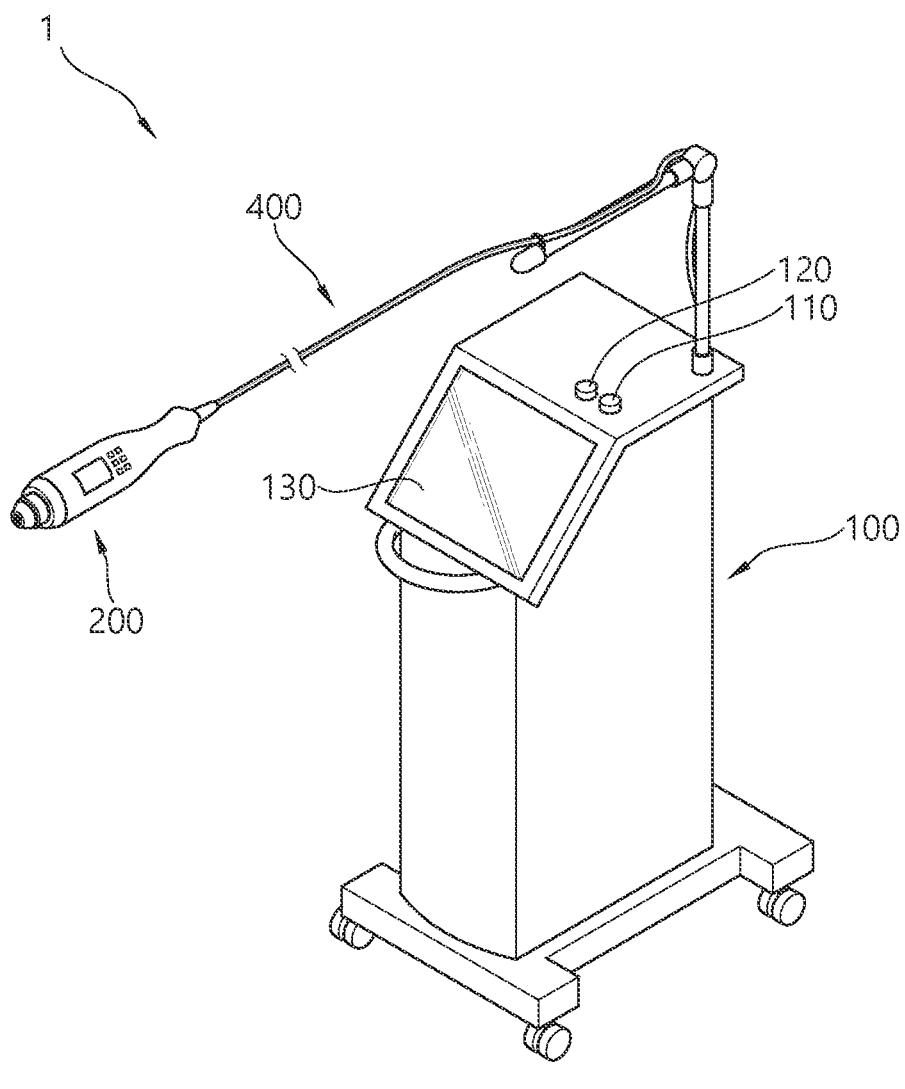

FIG. 8 is a perspective view of a radio frequency (RF) energy-based treatment device according to a second embodiment of the disclosure.

Figure 9:
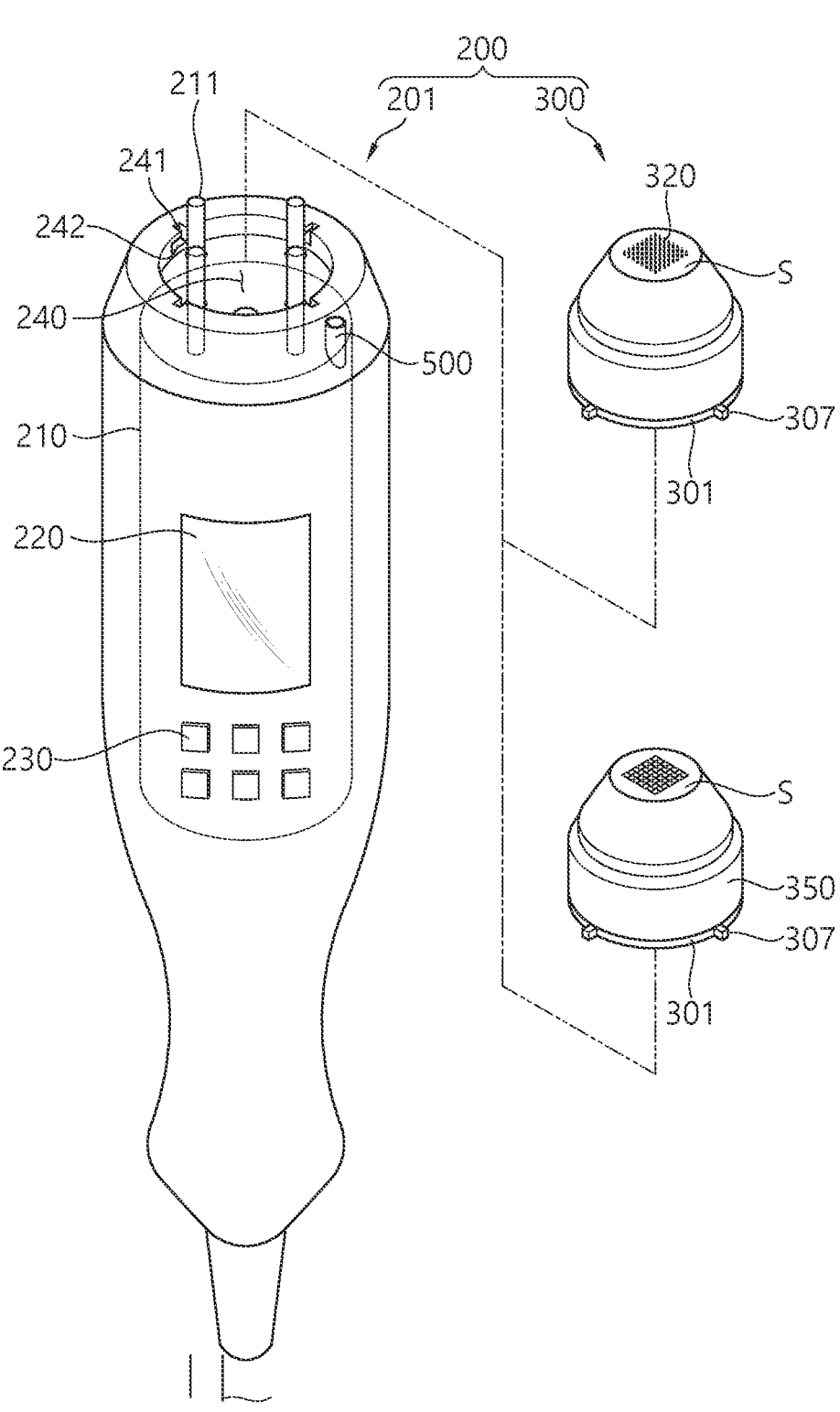

FIG. 9 is an enlarged perspective view of a handpiece in FIG. 8.

FIGS. 10A, 10B, 100 and 10D show states of use according to a second embodiment.

FIGS. 11A, 11B, 11C and 11D show states of use according to a second embodiment.

FIGS. 12A, 12B, 12C, 12D and 12E show alternative examples to the second embodiment.

Figure 13A:
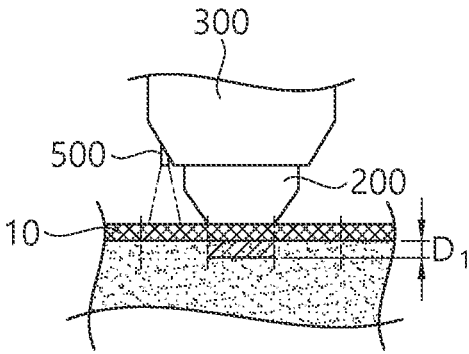
Figure 13B:
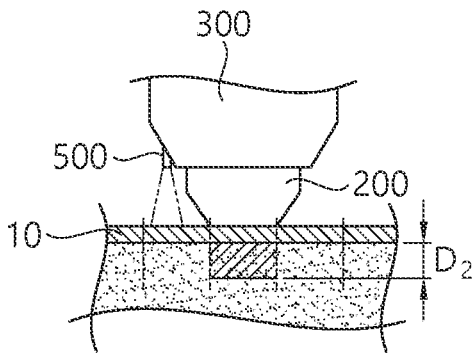

FIGS. 13A and 13B show states of use according to a third embodiment.

Figure 14:
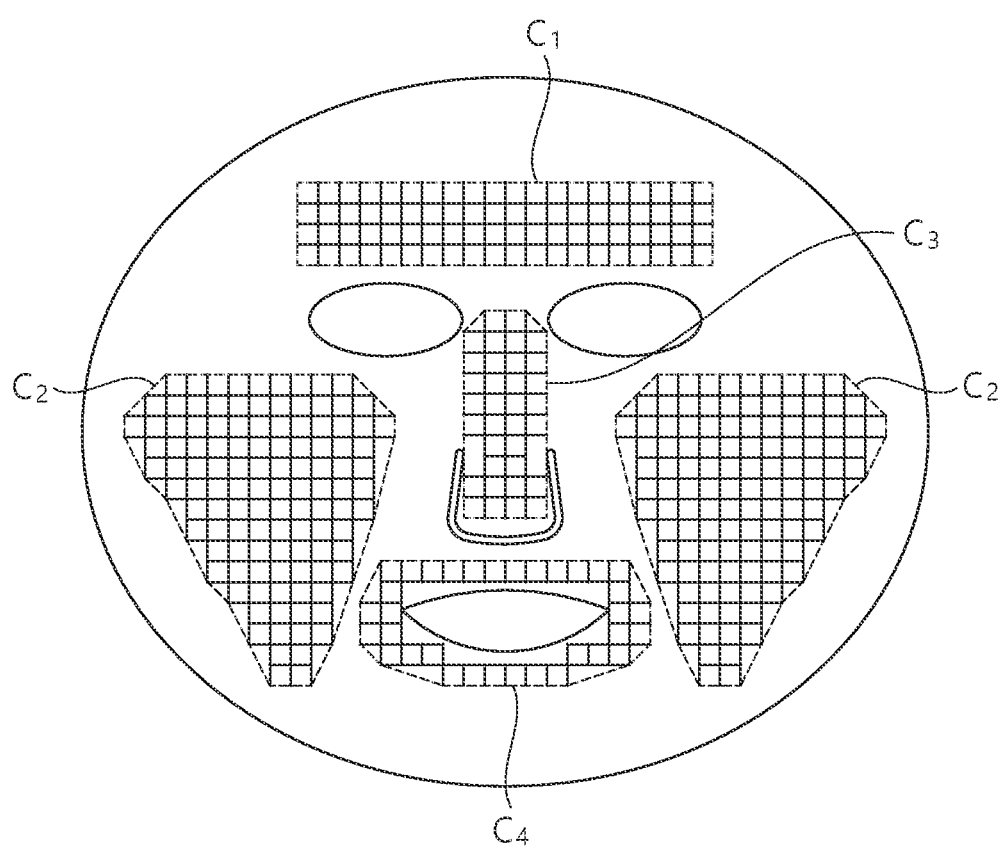

FIG. 14 is a conceptual view according to a fourth embodiment.

Figure 15:
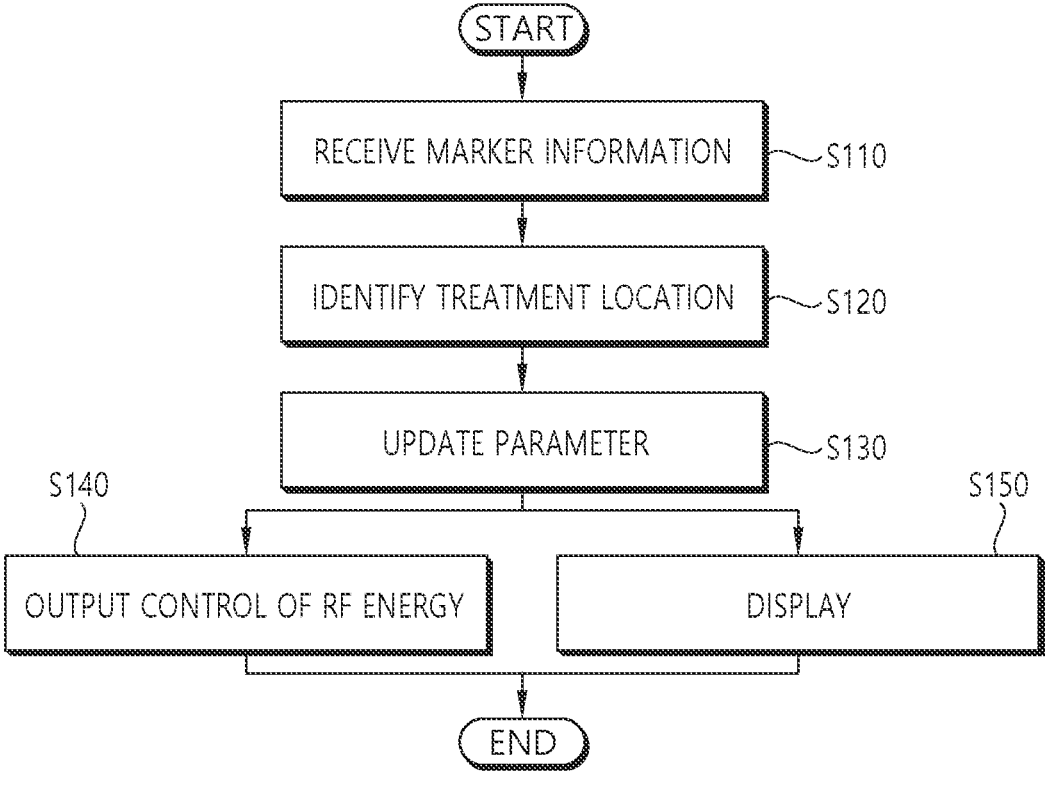

FIG. 15 is a flowchart showing a method of controlling an RF energy-based treatment device according to a fifth embodiment of the disclosure.

Figure 16:
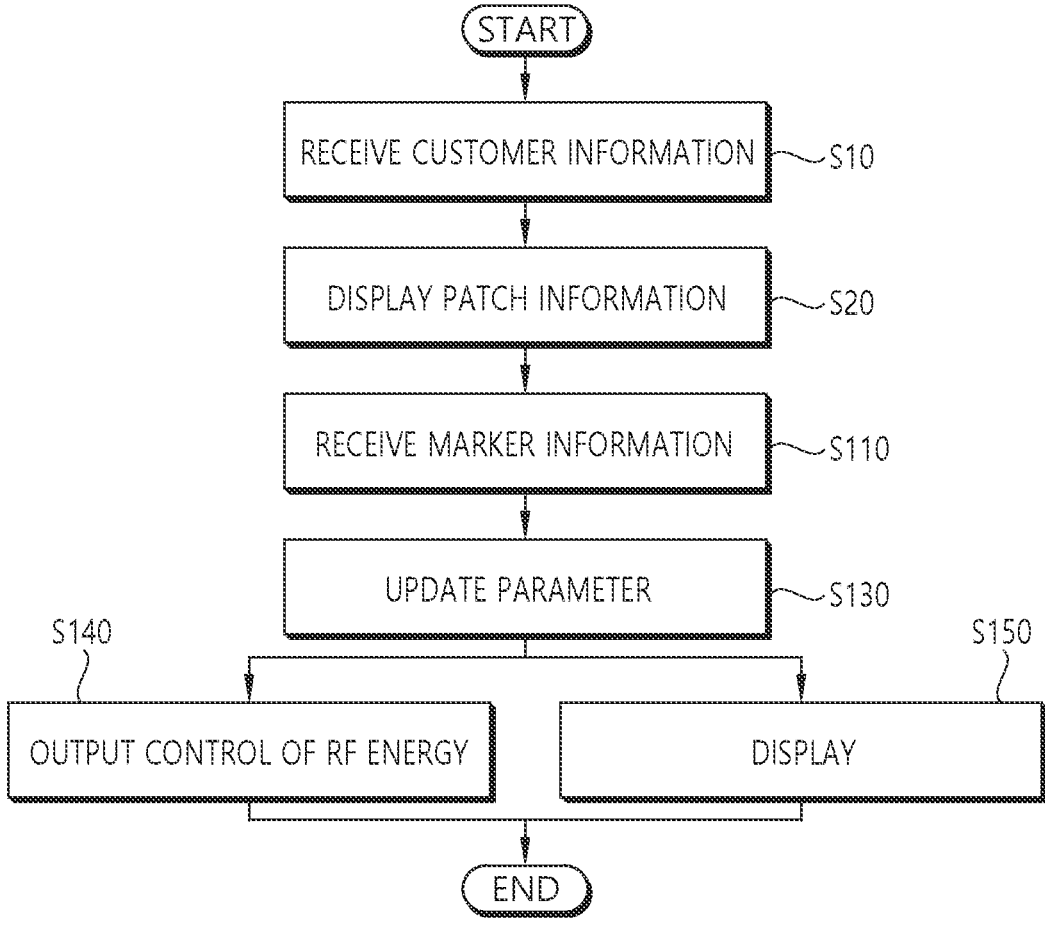
Figure 17:
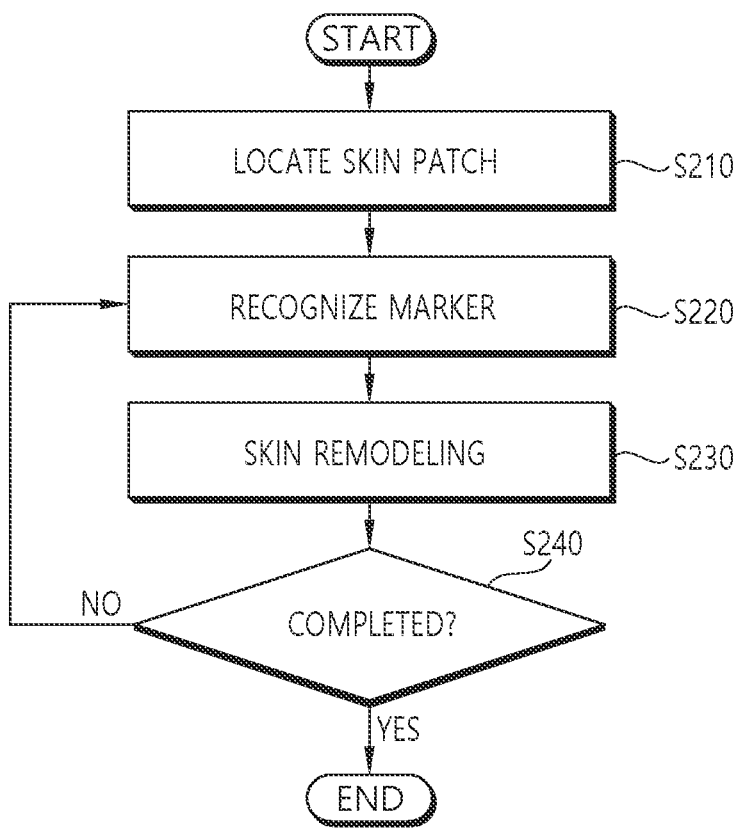

FIG. 16 shows an alternative example to the method of controlling the RF energy-based treatment device according to the fifth embodiment of the disclosure FIG. 17 is a flowchart showing an RF energy-based treatment method according to a sixth embodiment of the disclosure.

Figure 18:
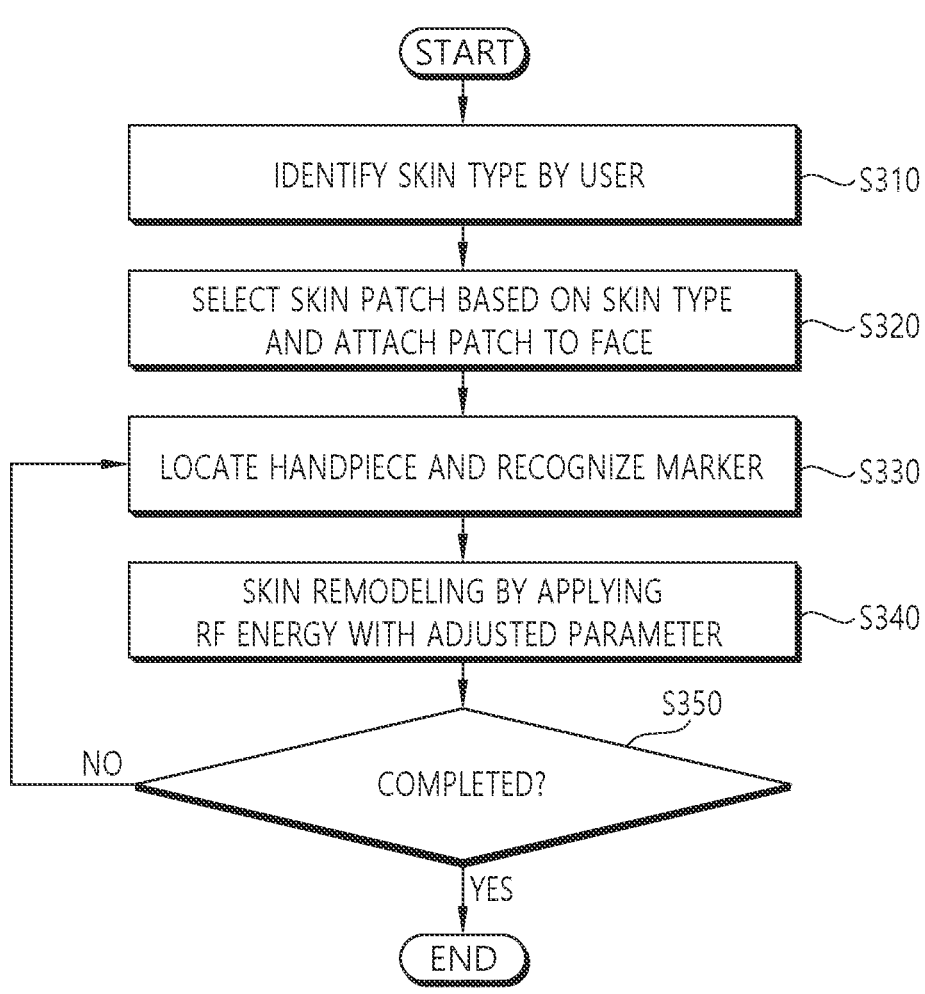

FIG. 18 shows an alternative example to the RF energy-based treatment method according to the sixth embodiment of the disclosure.

BEST MODE

Below, a skin patch for a radio frequency (RF) energy-based treatment device, an RF energy-based treatment device using the same, a method of controlling the same, and an RF energy-based skin treatment method according to embodiments of the disclosure will be described in detail with reference to the accompanying drawings. Elements described in embodiments set forth herein may be called other names in the art. However, if the elements are similar or identical in terms of their functions, they may be regarded as equivalents even in alternative embodiments. Further, symbols assigned to the elements are given for convenience of description. However, content on the drawings with these given signs do not limit the elements to a range in the drawings. Likewise, even though the elements on the drawings are partially modified according to alternative embodiments, they having functional similarity and identity may be regarded as equivalents. Further, if those skilled in the art recognizes natural involvement of elements, descriptions of the elements will be omitted.

Hereinafter, an 'RF treatment device' encompasses all devices for treating mammals including humans. The treatment device may include various devices for treatment, which transmits RF energy for the purpose of improving the condition of a lesion or tissue. In the following embodiments, descriptions will be made focusing on a device for treating a lesion of facial skin. However, the disclosure is not limited to these embodiments, and may be applied to lesions of various locations.

Further, hereinafter, treatment refers to remodeling of tissue into at least one of coagulation and ablation by transmitting RF energy to the tissue containing collagen, and may include treatment for at least one of wrinkles, tone and textural changes, scars and acne scarring, sagging mucosa, overall rejuvenation, hyperhidrosis, laxity, lifting, tightening, and fat reduction in skin tissue.

In addition, the treatment according to the disclosure will be described on the premise that the whole treatment region is treated by dividing a three-dimensionally formed treatment region into unit treatment areas, and treating the unit treatment areas one by one in sequence Below, a skin patch 10 according to the disclosure will be described in detail with reference to FIGS. 1 to 7.

Figure 1:
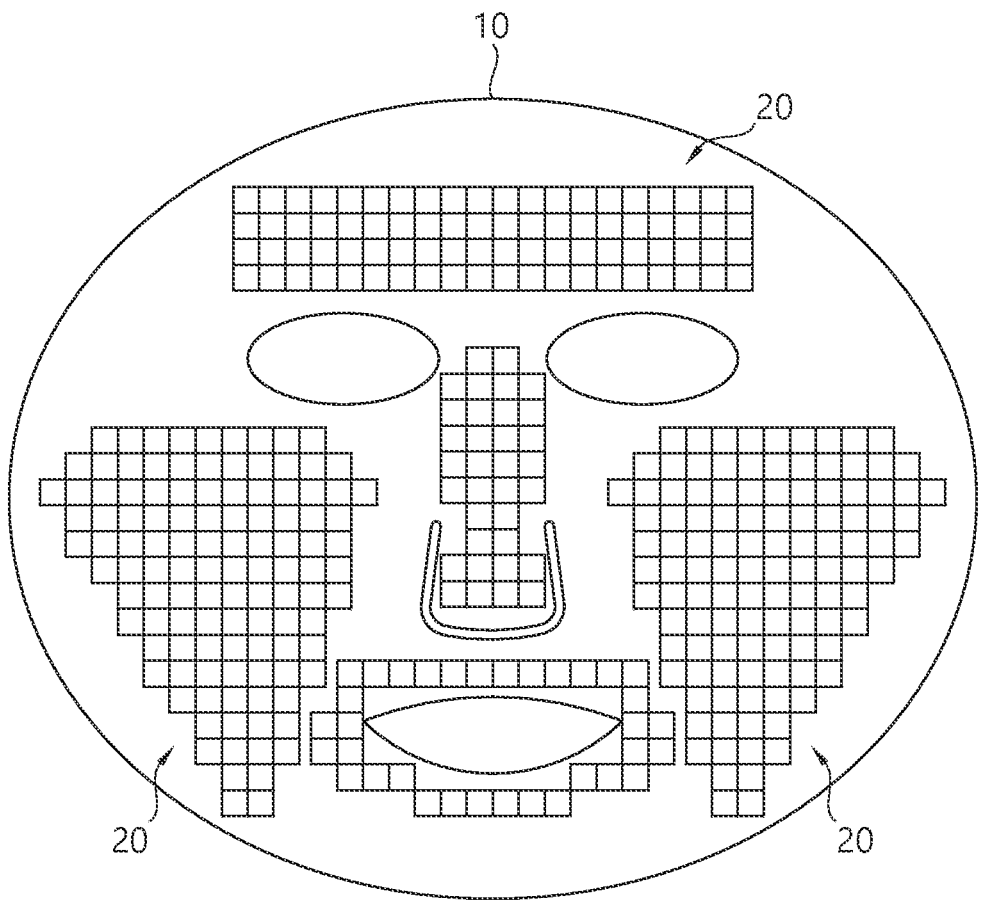
FIG. 1 is a conceptual view of a skin patch according to a first embodiment of the disclosure.

FIG. 1 is a conceptual view of the skin patch 10 according to a first embodiment of the disclosure. As shown therein, the skin patch 10 is provided to be used as attached to an appropriate location by a user when the RF treatment device is in use. Meanwhile, the skin patch 10 may be disposable to be thrown away after it is used once.

The skin patch 10 according to the disclosure is provided to have a first side to come into contact with and attached to skin, and a second side on which the RF energy-based treatment device is placed.

When the skin patch 10 is targeted for a face, the skin patch 10 may be shaped to cover the face including a treatment region. Further, the skin patch 10 may be cut out corresponding to parts that needs to be untreated, for example, eyes, a mouth and nostrils. The skin patch 10 may include a dielectric so that electric interaction can occur between the skin and an electrode of a handpiece while a skin treatment device using the RF energy (to be described later) is in use.

The skin patch 10 may include a marker 20 corresponding to the treatment region. The treatment region on the facial skin is divided into a region that is required to be remodeled by applying the RF energy, and a danger region that should not be damaged because nerves and blood vessels are present. The region required to be remodeled may be statistically determined from normal human faces.

The marker 20 may be provided so that a user can visually recognize the treatment region. The markers 20 may be provided corresponding to the treatment regions divided in the facial skin. The markers 20 may be provided to indicate a first treatment region corresponding to a forehead, a second treatment region corresponding to a right cheek, and a third treatment region corresponding to a left cheek.

The marker 20 helps a user to locate the handpiece at the unit treatment location, and may be configured to provide location information to be used when the RF energy-based treatment device is controlled. Meanwhile, details of the marker 20 will be described later with reference to FIGS. 2 to 4.

Meanwhile, although it is not shown, the skin patch 10 may be used while retaining a material in a fluid state. The material in the fluid state may include medicine that affects on skin, or a substance that acts on an electric characteristic between the electrode of the handpiece and the skin.

Figure 2:
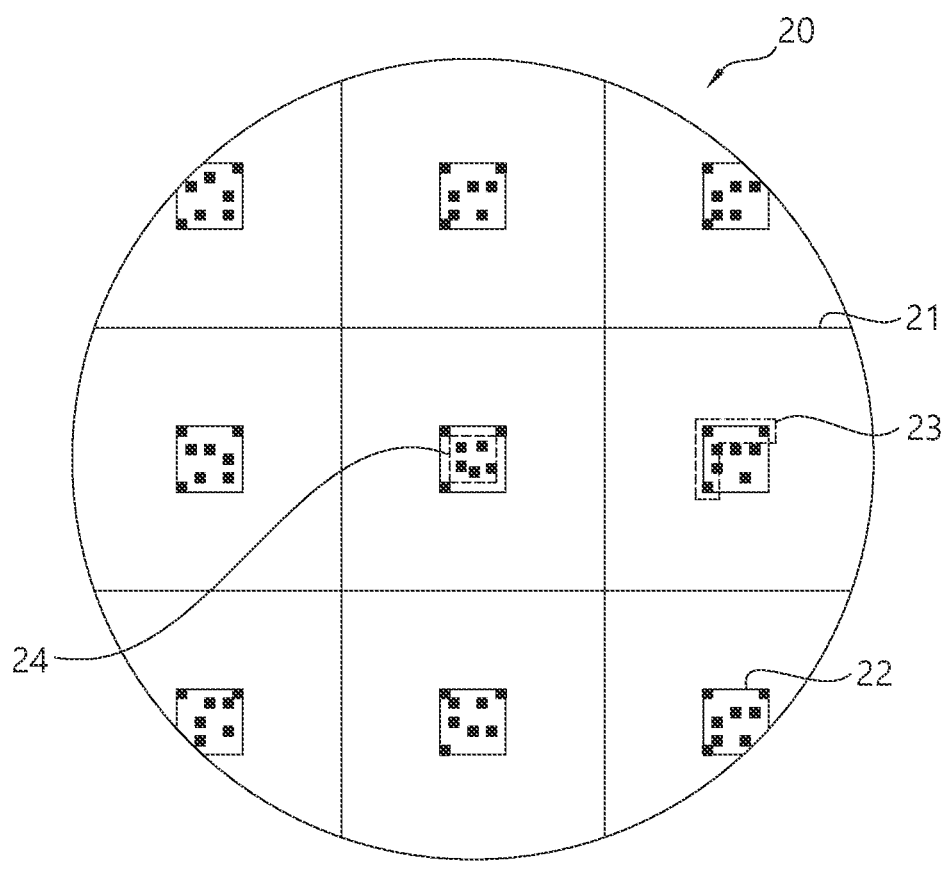
FIG. 2 is an enlarged conceptual view of some of markers shown in FIG. 1.

FIG. 2 is an enlarged conceptual view of some of the markers 20 shown in FIG. 1. As shown therein, the marker 20 provided in the skin patch 10 may include a unit region marker 21, and a recognition code 22.

The unit region marker 21 is configured to be visually recognized by a user and guides the user when the electrode of the handpiece is pushed against the patch. The unit region markers 21 are marked by dividing each treatment region into unit regions, each unit region corresponding to an area to which the treatment of the RF energy-based treatment device is applied once. For example, when the treatment of the RF energy-based treatment device is applied to a quadrangular region, the unit region marker 21 may be shaped like a quadrilateral. The unit region markers 21 may be marked to be in contact with each other so that an untreated portion can be minimized when the treatment of the RF energy-based treatment device is performed multiple times. For instance, the unit region markers 21 may be marked in a grid pattern. Therefore, the untreated portion is minimized when the treatment is performed along the unit region markers 21 while a user pushes the tip of the handpiece against the skin patch 10

The recognition code 22 may include unique information about the current location. The recognition code 22 may be marked in each unit region. The recognition code 22 may be marked in a boundary of the unit region, i.e., the unit region marker 21, or at the center portion of the unit region marker 21.

The handpiece recognizes the recognition code 22 marked on the unit region at which the electrode is currently located or another unit region adjacent to the unit region where the electrode is currently located, thereby recognizing the current location of the handpiece.

The recognition code 22 is configured to be recognized by a reader unit of the handpiece, and may for example include a code including two-dimensional information as shown in FIG. 2.

Figure 3:
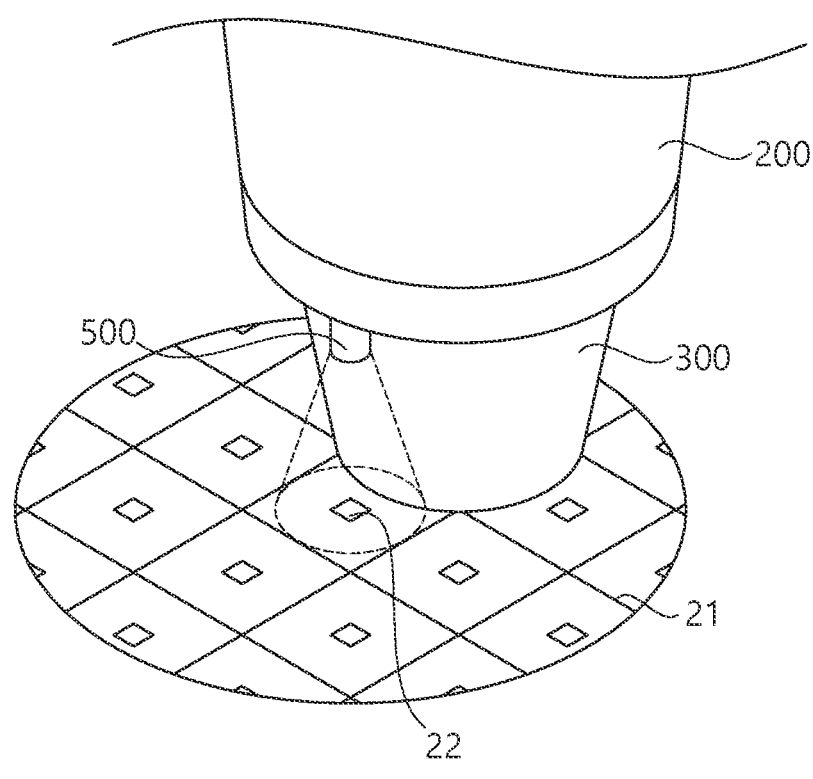
FIG. 3 shows a state of a skin patch in use.
Figure 4A:
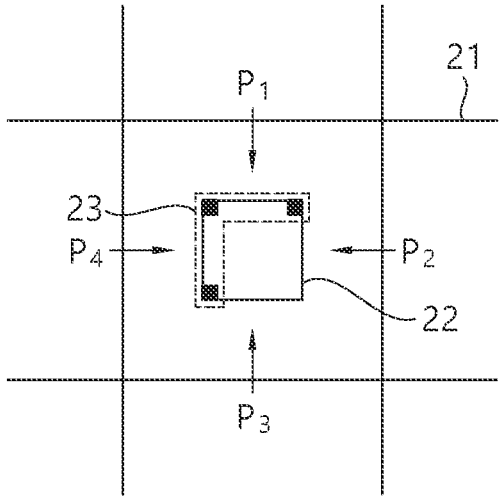
FIGS. 4A, 4B, 4C, 4D and 4E are conceptual views of recognizing a location from a marker.
Figure 4B:
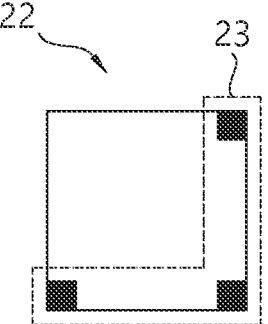
Figure 4C:
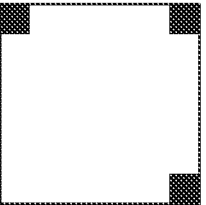
Figure 4D:
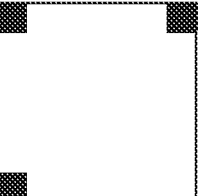
Figure 4E:
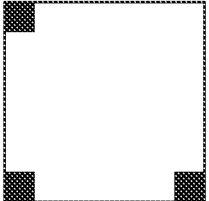

FIG. 3 shows a state of the skin patch 10 in use. Description of FIG. 3 will be made on the premise that the patch is being attached to the skin. For the treatment, the handpiece approaches from above the patch, and the electrode is aligned with and becomes in contact with the unit region marker 21. Then, the reader unit provided at one side of the handpiece is used to recognize the recognition code 22 marked on the unit region adjacent to the current treat region. The RF energy-based treatment device can identify the location of the current treatment region based on the recognized information.

Meanwhile, a user does not orient the handpiece in a specific direction, and it is therefore needed to accurately identify the current location regardless of the orientation of the handpiece. In this regard, descriptions will be made with reference to FIGS. 4A, 4B, 4C, 4D and 4E.

FIGS. 4A, 4B, 4C, 4D and 4E are conceptual views of recognizing the location from the marker 20. With reference to these drawings, it will be described that the location is identified in four unit regions adjacent to one recognition code 22. As shown therein, the recognition code 22 is configured to give two-dimensional information, and therefore the current treatment location is accurately identified even when only one recognition code 22 is recognized. For example, the recognition code 22 may include a quick response (QR) code.

The QR code or the like two-dimensional code includes a first pattern 23 for identifying the direction of the code, and a second pattern including the information. The RF energy-based treatment device identifies the current location by leading both the patterns.

Specifically, when the recognition code 22 is recognized as shown in FIGS. 4b to 4e when viewed from positions P1 to P4 at which the handpiece is located. Here, all the first patterns 23 of the recognition code 22 are set to point in one direction, and thus the current direction is calculated based on the currently recognized first pattern 23 with respect to the pointed direction. Further, the location, i.e., coordinate information of the unit region is read by recognizing the second pattern 24. Eventually, the first pattern 23 and the second pattern 24 are used to get information about the location and the direction, and therefore the current location of the handpiece is calculated.

FIG. 5 shows an alternative example to the markers 20 according to the first embodiment. As shown therein, the marker 20 may be configured in such a manner that the recognition codes 22 are combined to involve the unit region marker 21. In this example, the recognition code 22 is marked as a bar code. Even in this case, the directionality is given to the bar codes so that the current location and the current direction can be accurately recognized by reading only one barcode.

FIG. 6 is a conceptual view of another alternative example to the first embodiment. In this example, the skin patch 10 is configured to indicate whether the treatment of each unit region has been completed. In other words, the skin patch 10 may be configured to allow a user to visually recognize a treatment completion region At in person. Specifically, when the RF energy is used to treat skin, the skin patch 10 is configured to be partially changed in state due to the transfer of the energy. For example, the state change of the skin patch 10 may be directly caused by the RF energy, or may be caused by thermal energy generated by the transfer of the RF energy. The state change may for example include a change in color. However, this state change is merely given by way of example, and may include a visually recognizable change like a change in shape.

With the foregoing configuration according to this embodiment, it is possible to intuitively know the treatment location and whether the treatment has been completed, while looking at only the skin patch 10 without looking at the display of the RF energy-based treatment device.

FIG. 7 is a conceptual view of an alternative example to the first embodiment. This embodiment shows that the skin patch 10 is separated into a plurality of pieces. In this embodiment, the plurality of pieces are shaped to respectively correspond to the plurality of treatment regions, thereby making up a set. Although it is not shown, the piece corresponding to each treatment region may additionally include an identification code for recognizing the treatment region.

Below, the RF energy-based treatment device according to the disclosure will be described in detail with reference to FIGS. 8 to 11.

FIG. 8 is a perspective view of an RF energy-based treatment device according to a second embodiment of the disclosure, and FIG. 9 is an enlarged perspective view of a handpiece in FIG. 8.

In this embodiment, the RF treatment device refers to a device that transfers energy to the inside of skin tissue by inserting an insertion unit into the skin tissue of a human body. The insertion unit in the embodiment includes a plurality of needles, so that energy can be transferred to the inside of the skin tissue through the ends of the needles.

Specifically, the treatment device in this embodiment includes a main body 100, a handpiece 200 to be gripped by a user to carry out the treatment, and a connector 400 connecting the main body 100 and the handpiece 200.

The main body 100 may internally include an RF generator, and a controller (not shown). The controller generates a control input for controlling the RF generator based on a sensing value received from a sensor. In this case, the RF energy may be adjusted in frequency according to a patient's physical constitution, treatment purposes, treatment parts, etc. For example, the RF energy used in the skin treatment may be adjusted within a range from 0.1 to 10 MHz.

The main body 100 may externally include a switch 110 for power on/off, a frequency control lever 120 to adjust the frequency of the RF energy generated in the RF generator, and a display to display various pieces of information such as operation content of the treatment device. The display may be provided as a touch screen 130 allowing a user to input a command and displaying treatment information. The display may display a symbol shaped corresponding to the marker, and display an image for checking the current treatment location and whether the treatment has been completed.

Meanwhile, the handpiece 200 is connected to the main body 100 by the connector 400. The connector 400 can transfer the RF energy generated by the RF generator of the main body 100 to the plurality of needles 320, which corresponds to the insertion unit of the foregoing embodiment, and supply power needed for driving various elements of the handpiece from the main body. The connector 400 is provided in the form of a cable, and may use a cable including a plurality of conductive wires in which a metal wire is coated with insulation.

The handpiece 200 includes a housing in which an actuator 210 and a cooler 40 are placed. The actuator 210 is provided to make an output terminal 211, which is provided at one end of the actuator 210, linearly move in a lengthwise direction. As the output terminal 211 is linearly movable, the plurality of needles 320 provided at the end of the output terminal may retractably protrude outward from the contact surface of the handpiece. Therefore, the plurality of needles 320 is activated by the actuator 210 to be inserted into or pulled out of a patient's tissue. The actuator 210 may be provided as a linear actuator using a solenoid, a hydraulic/pneumatic cylinder, etc.

The handpiece 200 may externally include a handpiece controller 230, a handpiece display 220, and a reader unit 500. The handpiece controller 230 is provided to turn on/off the handpiece, adjust the depth at which the insertion unit 10 is inserted, adjust the amount of energy transferred through the insertion unit 10, etc. The handpiece display 220 may display a setting mode or various pieces of information needed during the treatment to a user. Therefore, a user can easily control the treatment content during the treatment through the handpiece controller 230, and easily grasp the treatment content through the handpiece display 220, while holding the handpiece in his/her hand.

The reader unit 500 is provided to check the markers marked on the foregoing skin patch. The reader unit 500 may be configured to read a direction in which the end, i.e., a tip module of the handpiece. For example, the reader unit 500 may be provided at a position for recognizing the marker adjacent to the treatment location when the handpiece is located at the treatment location. The reader unit 500 may be configured to read a bar code, a QR code and the like simple identification code, and detailed descriptions thereof will be omitted because such configuration has been widespread.

The handpiece includes a tip module 300, 350 at the end thereof. The tip module 300 may invasively be configured to include the plurality of needles 320 that penetrates the tissue, or may noninvasively be configured not to penetrate the tissue, and one of the tip modules 300 and 350 may be selected and detachably mounted to a handpiece main body 201. Specifically, the base 301 forms the bottom of the tip module, and includes detachment projections 307 protruding outward from an outer wall of the base 301. The base 301 may include hollows formed adjacent to the protruding portions of the needles and allowing cool air from the cooler to pass therethrough. Further, the base 301 may include a plurality of through holes so that the cool air can be discharged to the outer portions which are not adjacent to the protruding portions of the needles. In the handpiece, a recessed portion 240 to which the tip module is mounted is formed with a guide groove 241 for guiding the detachment projection 307, and a separation preventing groove 242 for preventing the detachment projection 307 guided along the guide groove 241 from being separated. In addition, the detachment projections 307 of the tip module are guided along the guide grooves 241 and fastened to the separation preventing grooves 242, so that the tip module can be mounted to the handpiece. Meanwhile, the tip module may be provided to seal up the inside/outside of the handpiece so as to prevent the cool air from leaking out and affecting the skin surface while the cooler is actuated to cool the needles 320. Here, the sealing allows a gap between the tip module and the handpiece as long as the cool air is prevented from leaking out and affecting the skin surface.

However, it is merely an example that the tip module in this embodiment is detachably mounted to the handpiece. Alternatively, the tip module and the handpiece may be formed as a single body.

Specifically, an electrode may include a micro electrode, the diameter of which approximates 5 to 500 μm. The electrode is made of a conductive material to transmit the RF energy. The surface of each electrode except a front end portion is made of an insulating material so as not to transfer the RF energy to the tissue. Thus, the front end portion of each needle partially serves as the electrode, so that the RF energy can be transmitted to the tissue through the front end portion. Therefore, the RF energy is selectively transferred to a part in which the end portion of the electrode is located during the treatment.

A front surface S of the tip module may form a portion to be adjacent to or come into contact with a patient's skin during the treatment, and includes a plurality of through holes through which a plurality of electrodes can appear and disappear.

The tip module includes at least one hole formed on the bottom thereof and allowing the output terminals 211 to pass therethrough. The output terminal 211 moves linearly along the hole during operation of the actuator 210, and presses against a substrate. The substrate includes a rear side to be seated on a supporter inside the tip module, and a front side to be pressed by an elastic member provided inside the tip module. When the output terminal 211 moves and pushes the substrate, the substrate is separated from the supporter and moves forward, and the plurality of electrodes 320 protrudes from the front of the through holes and enters into the skin tissue. Further, when the output terminal 211 moves backward by the operation of the actuator 210, the substrate moves backward due to the restoring force of the elastic member and the plurality of electrodes 320 also returns to the inside of the tip module. Although it is not separately shown, an additional guide member may further be provided to make the supporting plate move along a guided path.

Although is it not specifically illustrated, the circuit of the substrate may be provided to be electrically connected to the RF generator of the main body when the tip module is mounted to the handpiece. Alternatively, the circuit of the supporting plate may be provided to be selectively and electrically connected to the RF generator when the supporting plate is pressed by the output terminal 211 (for example, the electrode 320 is formed at the end portion of the output terminal and electrically connected to the supporting plate when pressed).

Below, use of the RF energy-based treatment device according to the disclosure will be described in detail with reference to FIGS. 10A to 12E.

FIGS. 10A to 11D show states of use according to a second embodiment, and FIGS. 12A to 12E show alternative examples to the second embodiment. The second embodiment shows an example that the electrode is a non-penetrating type. FIGS. 10A to 11D show the location and operation of the handpiece, and content displayed on the display according to the location and operation of the handpiece. The display may display symbols 131 shaped corresponding to the markers 20, and a plurality of unit treatment-region symbols 132 corresponding to one treatment region.

Figure 10A:
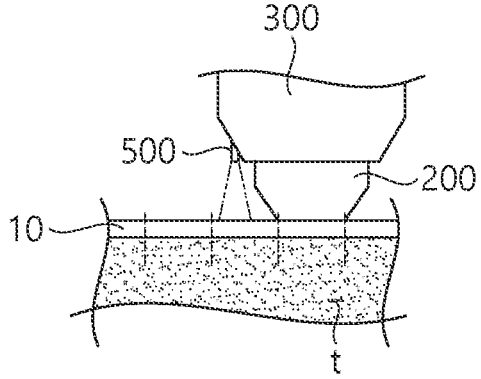
Figure 10B:
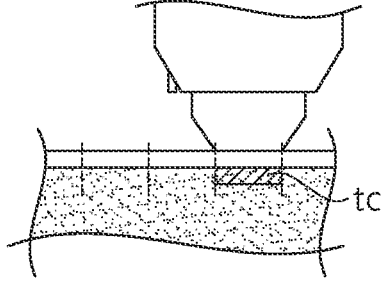
Figure 10C:
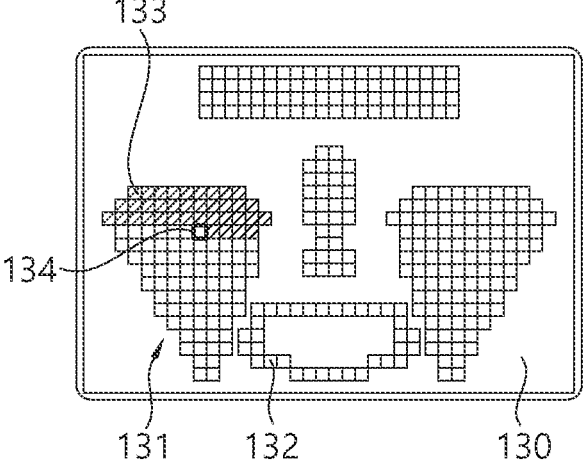
Figure 10D:
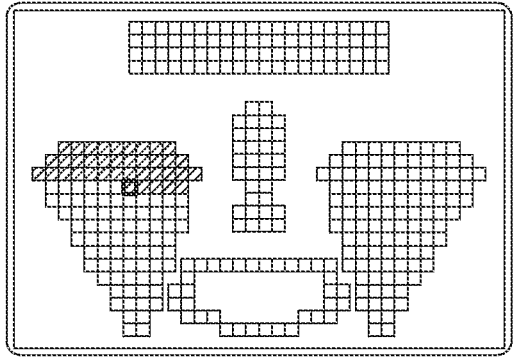

As shown in FIG. 10A, when the handpiece is located at a certain treatment location, the reader unit 500 is first used to recognize the marker 20. Then, the controller recognizes the marker 20 and identifies the current treatment location. Then, as shown in FIG. 100, the controller controls a display 130 to display current treatment region symbols 134 with regard to the treatment region corresponding to the current location. Then, when the RF energy is applied to tissue t as shown in FIG. 10B, the tissue in the corresponding region is treated, and the controller controls a treatment completion region symbol 133 to be displayed inside the current treatment region symbol 134 corresponding to the location of the treated tissue tc as shown in FIG. 10D.

Figure 11A:
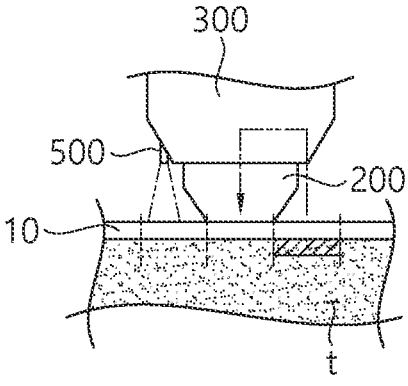
Figure 11B:
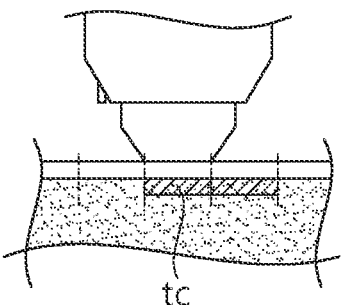
Figure 11C:
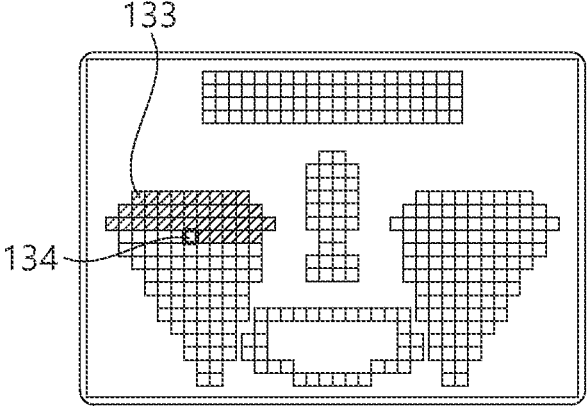
Figure 11D:
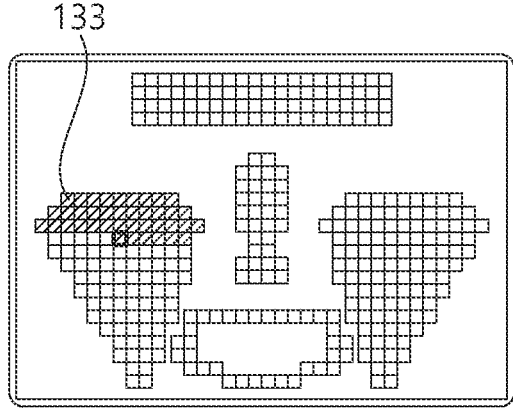

Then, when a user relocates the handpiece by changing the treatment location as shown in FIG. 11A, the marker 20 is recognized again, and the controller identifies the current treatment location based on the information of the recognized marker 20 and controls the display to display the current treatment region symbol 134 as shown in FIG. 11B. Then, the RF energy is applied to treat the tissue t as shown in FIG. 11C, and the treatment completion region symbol 133 is displayed inside the current treatment region symbol 134 as shown in FIG. 11D.

Meanwhile, when the RF energy-based treatment device automatically recognizes the current treatment location before starting the treatment, control may be made so that the treatment varied depending on the locations can be performed with a preset value based on the automatically recognized current treatment location. For example, the skin of the first treatment region including the forehead is thinner than the skin of the second treatment region including the cheek. Thus, the RF energy needs to be adjusted corresponding to the thickness of the skin, so as to have uniform treatment effect even though the skin is varied in thickness. To this end, the handpiece scans the markers 20 to identify the treatment location, and the RF energy is applied while updating a value of a preset parameter based on the identified treatment location.

With this configuration of the RF energy-based treatment device, a user can easily change the location by the guidance of the markers 20 when the location change is repetitively needed, and the RF energy according to the locations is easily controlled because information about the corresponding treatment location is automatically recognizable.

Figure 12A:
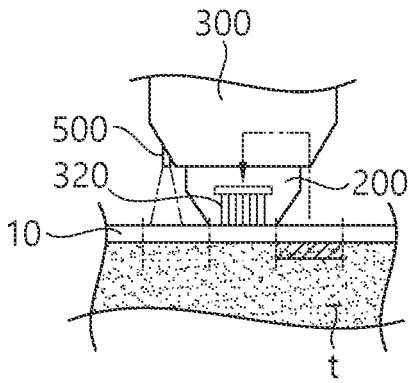
Figure 12B:
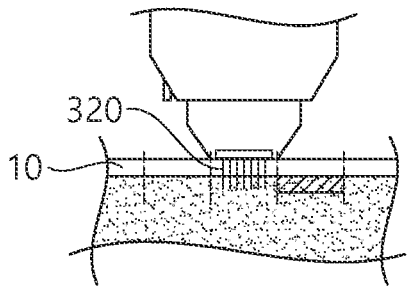
Figure 12C:
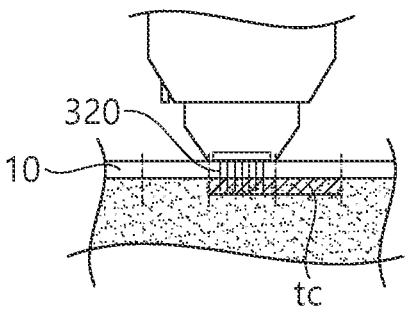
Figure 12D:
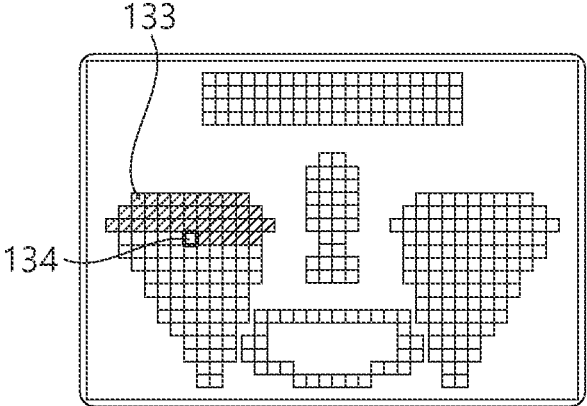
Figure 12E:
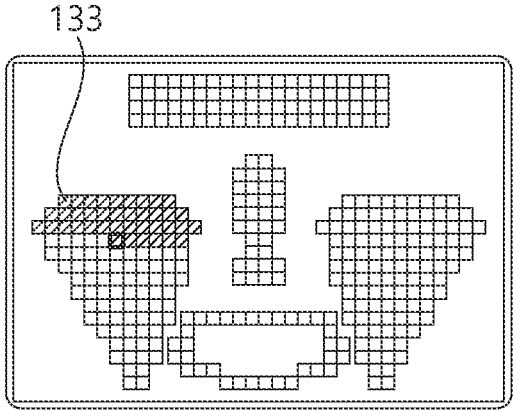

Referring back to FIGS. 12A to 12E, an embodiment is illustrated with a penetrating-type electrode. FIG. 12A shows that the handpiece is moved left after some regions are treated in a previous stage. Like the foregoing embodiment, the handpiece is located on the patch, recognizes the marker, and loads the current location information. Then, as shown in FIG. 12B, the penetrating-type electrode is inserted into the tissue. Then, as shown in FIG. 12C, the parameter of the RF energy is adjusted based on the information recognized from the marker, and the RF energy is applied so as to treat the tissue. In this regard, displayed images are shown in FIGS. 12D and 12E, and the displayed images may be configured in the same manner as those according to the embodiment shown in FIGS. 11c and 11d.

Below, a third embodiment will be described in detail with reference to FIGS. 13a and 13b.

FIGS. 13a and 13b show states of use according to a third embodiment. Descriptions of FIGS. 13a and 13b will be made on the premise that a dielectric characteristic of a patch is used to adjust the RF energy transferred to the tissue, and the RF energy-based treatment device has a non-penetrating type electrode. As shown therein, the patch may be provided to have a predetermined dielectric constant. There may be a plurality of patches of which dielectric constants are different from one another. When customers (patients) are different in skin characteristics, skin types may be determined by distinguishing certain ranges. A user can select a patch having an appropriate dielectric constant based on the skin type of the customer, and attach the selected patch to the customer's skin. In this embodiment, the marker may include information about the kinds of patches. Therefore, when the marker is recognized by a scanner, the kind of patch and the current treatment location may be identified. In this case, the markers may be differently provided according to the pieces of information, and include a maker including the information about the kind of patch, and a marker including the location information. Alternatively, the marker including the location information may also include the current patch information.

Referring back to FIGS. 13A and 13B, the patch 10 shown in FIG. 13A and the patch 10 shown in FIG. 13B are different in a dielectric constant from each other, and the treatment aspect may be varied depending on the dielectric constants of the patch. Therefore, a user can select the patch having an appropriate dielectric constant based on a calculated value, and use the selected patch for the treatment. When a plurality of patches are different in dielectric constant, the treatment aspect may vary even though the same RF energy is applied. For example, varying treatment aspects may include treatment depths D1 and D2, and tissue degeneration.

Below, a fourth embodiment will be described with reference to FIG. 14. FIG. 14 is a conceptual view according to the fourth embodiment. As shown therein, a patch according to the disclosure may be divided into a plurality of regions, and the plurality of regions may be configured in such a manner that at least one region is different in dielectric constant from another region. In case where the regions of the patch are different in dielectric constant, different treatment aspects may be caused according to the regions of the patch when the RF energy is applied between the electrode of the handpiece and the tissue. Therefore, the regions of the patch different in dielectric constant are appropriately selected to have the maximum treatment effects as desired. For example, a material for a cheek region C2 may be selected to have a lower dielectric constant than that for a forehead region C1, and a material for a nose region C3 may be selected to have a higher dielectric constant than that for that for a region around a mouth C4. However, the foregoing relative comparison in dielectric constant is merely an example, and regions different in dielectric constant may be variously combined. Therefore, the RF energy-based treatment device recognizes the marker and recognizes information about the current region.

Below, a method of controlling an RF energy-based treatment device according to a fifth embodiment of the disclosure will be described with reference to FIGS. 15 and 16. This embodiment may be implemented by the controller of the foregoing RF energy-based treatment device or the like computable processor.

FIG. 15 is a flowchart showing the method of controlling the RF energy-based treatment device according to the fifth embodiment of the disclosure. As shown therein, the method of controlling the RF energy-based treatment device according to the disclosure may include the steps of receiving information from the marker (S110), identifying a treatment location (S120), updating a parameter (S130), controlling an output of RF energy (S140), and displaying (S150).

The step of receiving information from the marker (S110) refers to the step of, by the reader unit provided in the handpiece, recognizing the marker of the skin patch attached to skin. In this step, the information is obtained from the recognition code of the marker by recognizing the marker.

The step of identifying the treatment location (S120) refers to the step of identifying the location of the current handpiece based on the information from the marker. The treatment region may be divided into a plurality of unit regions, and each unit treatment region AO may be provided with the marker having unique information. Therefore, when a certain marker is recognized, the current location is accurately identified.

The step of updating the parameter (S130) refers to the step of adjusting the parameter so that appropriate treatment can be performed according to predetermined characteristics of the tissue t. The skin tissue t may be varied in characteristic depending on the locations. For example, a forehead and the like tissue t adjacent to a frontal bone, a cheekbone and the like bones may be different in electric characteristics from a cheek skin adjacent to muscles. Therefore, when the location is recognized, the parameter is updated so that the treatment optimized for each location can be performed. In this case, the parameter may be determined based on a experimentally predetermined value for each location. The parameter is set to adjust the output of the RF energy when the RF energy is controlled. The parameter may for example be set to adjust the pulse, frequency, pulse applying time, pulse period, voltage, current, total treatment time, etc. of the RF energy.

The step of controlling the output of the RF energy (S140) refers to the step of applying the RF energy to the handpiece based on the updated parameter. When the RF energy is applied to the electrode of the handpiece, the RF energy is transferred into the skin tissue t and the treatment is treated.

The step of displaying (S150) refers to the step of displaying information related to the current treatment. In the displaying step, various symbols by which the current treatment location and the treatment status so far are checkable are displayed. The displaying step may include displaying the symbols corresponding to the treatment region. Specifically, information by which the states of the whole treatment region, the current treatment region, the treatment completion region At, and the like treatment region are visually checkable according to the locations is displayed.

Meanwhile, the foregoing method of controlling the RF energy-based treatment device may be performed including the step of receiving the information from the marker to the displaying step with respect to one treatment region, and may be repeated until the treatment for the whole regions is entirely completed. Further, information obtained during the treatment procedure, i.e., a patient's information and treatment information are collected, and subsequent treatment may be performed based on the collected information. Here, a patient's information may for example include a patient's age, sex, skin tone, tissue impedance, etc. Further, the treatment the information may for example include the kind of patch, transferred RF energy, total RF energy, treatment period, etc.

FIG. 16 shows an alternative example to the method of controlling the RF energy-based treatment device according to the fifth embodiment of the disclosure As shown therein, the fifth embodiment may further include the steps of receiving information about a customer (patient) (S10), and displaying information about the patch (S20).

The step of receiving the information about the customer (patient) (S10) refers to the step of receiving a patient's current information before the treatment. The customer's information may include information about a certain skin type determined by a preset classification criterion based on at least one of data such as impedance monitoring, treatment and recovery aspects, which are obtained by using the RF treatment device.

The step of displaying the information about the patch (S20) refers to the step of selecting an appropriate patch to have the maximum treatment effects according to the purposes by taking the customer's information into account, and suggesting the selected patch to a user. Here, the plurality of patches may have dielectric constants different according to the kinds. Further, one patch may have various dielectric constants different according to its regions. Therefore, a suggestion is made on the display so that a user can select the patch optimized for the customer and the purpose of treatment among the plurality of patches.

Then, the step of receiving the information from the marker (S110) may be performed by automatically recognizing the marker on the patch when a user locates the handpiece at the treatment location while the patch is being currently attached to the skin of the customer. Here, the marker information may include the kind of current patch and the current treatment location. The markers may be differently provided to include the information about the kind of current patch and the information about the current treatment location, respectively. Alternatively, such pieces of information may be included in one marker.

Below, an RF energy-based treatment method according to a sixth embodiment of the disclosure will be described with reference to FIGS. 17 and 18.

FIG. 17 is a flowchart showing an RF energy-based treatment method according to a sixth embodiment of the disclosure.

As shown therein, the RF energy-based treatment method according to the disclosure may include the steps of locating the skin patch (S210), recognizing the marker (S220), and remodeling the skin (S230).

The step of locating the skin patch (S210) refers to the step of attaching the skin patch including the markers to the skin that needs to undergo the treatment. The skin may include various body parts, for example, facial skin.

The step of recognizing the marker (S220) refers to the step of, by the RF energy-based treatment device, recognizing the markers marked on the skin patch to input the current treatment location to the treatment device. The skin patch includes the markers by which the treatment region is divided into the unit treatment regions, i.e., regions, each of which is treated using the RF energy-based treatment device once. The step of recognizing the marker refers to the step of automatically recognizing the current location as one of the markers is recognized. A user locates the handpiece of the RF energy-based treatment device at the treatment location, and uses the reader unit provided in the handpiece, thereby recognizing the marker.

The step of remodeling the skin (S230) refers to the step of remodeling the skin by applying the RF energy to the skin. The remodeling means the degeneration of the tissue t as the RF energy is applied to the tissue. The RF energy, to which the updated parameter is applied, may be controlled to be applied to the tissue t.

Meanwhile, the foregoing steps of recognizing the marker (S210) to remodeling the skin (S230) may be performed with regard to one unit treatment region at a time, and may be repeated while relocating the handpiece of the RF energy-based treatment device until the treatment for the whole regions is entirely completed (S240). When the treatment for the whole regions is completed, the skin patch is taken off and the treatment is finished.

FIG. 18 shows an alternative example to the RF energy-based treatment method according to the sixth embodiment of the disclosure.

As shown therein, the alternative example to the sixth embodiment may include the steps of identifying a patient's skin type (S310), selecting the skin patch based on the skin type and attaching the selected skin patch to a face (S320), locating the handpiece and recognizing the marker (S330), and performing skin remodeling by adjusting the parameter and applying the RF energy (S340).

The step of identifying the patient's skin type (S310) refers to the step of identifying the skin type based on a user's current conditions, which is identified based on information about at least one of the user's skin tone, skin conditions, age, impedance of skin tissue, and treatment recovery aspects. Based on this information, a patient's skin type is classified according to a predetermined criterion.

The step of selecting the skin patch based on the skin type and attaching the selected skin patch to a face (S320) refers to the step of selecting and attaching the skin patch so that desired treatment can be implemented according to the skin types of the patient. A plurality of skin patches may be provided, and they may have different dielectric constants, respectively. Here, the selection of the skin patch based on the skin type may be performed by selecting the patch computed and suggested by the controller of the RF energy-based treatment device.

The step of locating the handpiece and recognizing the marker (S330) refers to the step of, by a user, locating the handpiece at the patch attached to the patient's skin and recognizing the location. When a user locates the handpiece at one of the treatment locations, the RF energy-based treatment device naturally recognizes the marker, and identifying the dielectric constant of the current patch and the current treatment location on the patch.

The step of performing the skin remodeling by adjusting the parameter and applying the RF energy (S340) refers to the step of applying the RF energy from the RF energy-based treatment device to the tissue. The RF energy-based treatment device adjusts the parameter for controlling the RF energy based on the information corresponding to the current treatment location, and the patch's dielectric constant.

Meanwhile, the foregoing steps of locating the handpiece and recognizing the maker (S330) and performing the skin remodeling by adjusting the parameter and applying the RF energy (S340) may be repeated until the treatment for the whole regions is entirely completed.

As described above, the skin patch 10 for the RF energy-based treatment device, the RF energy-based treatment device using the same, the method of controlling the same, and the RF energy-based skin treatment method can guide a user's treatment location based on a patch attached to skin, and control the RF energy based on the location information, thereby having effects on improving accuracy of treatment.

The invention claimed is:

1. A skin patch comprising:
a first side provided to come into contact with a skin, and
a second side provided to be usable while being in contact with an electrode of a radio frequency (RF) energy-based treatment device,
a marker provided to guide treatment of the RF energy-based treatment device,
wherein the marker comprises a plurality of unit region markers dividing a treatment region into a plurality of unit regions, each of the plurality of unit regions including a recognition code,
wherein the plurality of unit regions includes a first unit region in which the electrode of the RF energy-based treatment device is located to perform the treatment of the RF energy-based treatment device, and a second unit region adjacent to the first unit region, the recognition code of the second unit region identifying the first unit region, and
wherein the recognition code of the second unit region includes a first pattern identifying a direction of the recognition code in the second unit region, and a second pattern identifying coordinate information of the first unit region.

2. The skin patch according to claim 1, wherein the marker is provided to guide a treatment location of the RF energy-based treatment device.

3. The skin patch according to claim 2, wherein the marker comprises a plurality of unit region markers, each size of which corresponds to an area to which treatment of the RF energy-based treatment device is applied once.

4. The skin patch according to claim 2, wherein the recognition code is configured to be recognizable by the RF energy-based treatment device.

5. The skin patch according to claim 4, wherein the recognition code comprises a plurality of unique patterns configured to display unique information based on a location of the unit region marker.

6. The skin patch according to claim 2, wherein the skin patch comprises a dielectric.

7. The skin patch according to claim 6, wherein
the skin patch is divided into a plurality of regions, and
at least one among the plurality of regions is configured to have a different dielectric constant.

8. The skin patch according to claim 2, wherein the skin patch is provided to be attached to a region comprising at least a portion of a forehead and a cheek.

9. The skin patch according to claim 8, being disposable.

10. The skin patch according to claim 2, being provided to make state change in a region with which the RF energy-based treatment device comes into contact and to which treatment is applied.

11. The skin patch according to claim 10, wherein the state change comprises change in color to be visually recognizable.

12. The skin patch according to claim 1, wherein the first pattern indicates a moving direction of the RF energy-based treatment device from the first unit region to the second unit region.

13. The skin patch according to claim 1, wherein the skin patch is provided as a plurality of patches having different dielectric constants, and each of the plurality of unit region markers includes information of types of the plurality of patches.

* * * * *